(12) United States Patent
Cravo et al.

(10) Patent No.: US 9,284,329 B2
(45) Date of Patent: Mar. 15, 2016

(54) THIENOPYRIDONE DERIVATIVES USEFUL AS ACTIVATORS OF AMPK

(71) Applicant: POXEL, Lyons (FR)

(72) Inventors: Daniel Cravo, Montesson (FR); Sophie Hallakou-Bozec, Antony (FR); Sébastien Bolze, Massieux (FR); Franck Lepifre, Saclay (FR); Laurent Faveriel, Longjumeau (FR); Jean-Denis Durand, Montreuil-sous-Bois (FR); Christine Charon, Gometz-le-Châtel (FR)

(73) Assignee: POXEL, Lyons (FR)

( * ) Notice: Subject to any disclaimer, the term of this patent is extended or adjusted under 35 U.S.C. 154(b) by 0 days.

(21) Appl. No.: 14/411,690

(22) PCT Filed: Jun. 28, 2013

(86) PCT No.: PCT/EP2013/063741
§ 371 (c)(1),
(2) Date: Dec. 29, 2014

(87) PCT Pub. No.: WO2014/001554
PCT Pub. Date: Jan. 3, 2014

(65) Prior Publication Data
US 2015/0166566 A1     Jun. 18, 2015

(30) Foreign Application Priority Data

Jun. 29, 2012   (EP) .................... 12305775

(51) Int. Cl.
*C07D 495/04* (2006.01)
(52) U.S. Cl.
CPC .................... *C07D 495/04* (2013.01)
(58) Field of Classification Search
None
See application file for complete search history.

(56) References Cited

U.S. PATENT DOCUMENTS

| 7,119,205 B2 | 10/2006 | Iyengar et al. |
| 2005/0038068 A1 | 2/2005 | Iyengar et al. |
| 2006/0287356 A1 | 12/2006 | Iyengar et al. |
| 2011/0034505 A1 | 2/2011 | Cravo et al. |

FOREIGN PATENT DOCUMENTS

WO   WO 2009/124636   10/2009

OTHER PUBLICATIONS

International Search Report for PCT/EP2013/063741, mailed Jul. 30, 2013, Johnson, Claire, 2 pages.
Written Opinion of the International Searching Authority for PCT/EP2013/063741, mailed Jul. 30, 2013, Johnson, Claire, 4 pages.

*Primary Examiner* — Timothy R Rozof
(74) *Attorney, Agent, or Firm* — Nixon & Vanderhye P.C.

(57) ABSTRACT

Activators of AMPK and therapeutic uses thereof The invention relates to compounds that are direct activators of AMPK (AMP-activated protein kinase) and their use in the treatment of disorders regulated by activation of AMPK. For instance, compounds according to the invention are useful for the treatment of diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies.

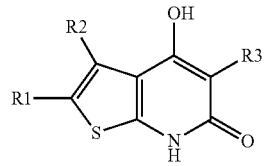

(1)

10 Claims, No Drawings

THIENOPYRIDONE DERIVATIVES USEFUL AS ACTIVATORS OF AMPK

This application is the U.S. national phase of International Application No. PCT/EP2013/063741, filed 28 Jun. 2013, which designated the U.S. and claims priority to EP Application 12305775.4, filed 29 Jun. 2012; the entire contents of each of which are hereby incorporated by reference.

The invention relates to compounds that are direct activators of AMPK (AMP-activated protein kinase) and their use in the treatment of disorders regulated by activation of AMPK. For instance, compounds according to the invention are useful for the treatment of diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies.

BACKGROUND AND INTRODUCTION TO THE INVENTION

AMPK is well established as a sensor and regulator of cellular energy homeostasis. Allosteric activation of this kinase due to rising AMP levels occurs in states of cellular energy depletion. The resulting serine/threonine phosphorylation of target enzymes leads to an adaptation of cellular metabolism to low energy state. The net effect of AMPK activation induced changes is inhibition of ATP consuming processes and activation of ATP generating pathways, and therefore regeneration of ATP stores. Examples of AMPK substrates include acetyl-CoA carboxylase (ACC) and HMG-CoA reductase. Phosphorylation and therefore inhibition of ACC leads to simultaneous decrease in fatty acid synthesis (ATP-consuming) and increase in fatty acid oxidation (ATP-generating). Phosphorylation and resulting inhibition of HMG-CoA reductase leads to a decrease in cholesterol synthesis. Other substrates of AMPK include hormone sensitive lipase, glycerol-3-phosphate acyltransferase, malonyl-CoA decarboxylase.

AMPK is also involved in the regulation of liver metabolism. Elevated glucose production by the liver is a major cause of fasting hyperglycemia in type 2 diabetes (T2D). Gluconeogenesis in the liver is regulated by multiple enzymes such as phosphoenolpyruvate carboxykinase (PEPCK) and glucose-6-phosphatase—G6Pase. Activation of AMPK suppresses the transcription of theses genes in hepatoma cells.

AMPK activation also down-regulates gluconeogenesis acting on some other genes expression. These effects may be due to its ability to down-regulate key transcription factors such as SREBP-1c, ChREBP, or HNF-4alpha or to direct phosphorylate transcriptional coactivators such as p300 or TORC2.

AMPK is considered as an attractive candidate for contraction-induced skeletal muscle glucose uptake because it is activated in parallel with elevation in AMP and a reduction in creatine phosphate energy stores. Furthermore, AICAR-induced activation of AMPK increases glucose uptake concomitantly with glucose transporter 4 (GLUT4) fusion with plasma membrane. Over-expression of an alpha2 kinase dead subunit in skeletal muscle abolishes AICAR, but partially impairs contraction-stimulated glucose uptake. These findings suggest that additional pathways mediate contraction induced glucose uptake, whereas it is clear that AMPK mediates the effects of AICAR on glucose uptake.

Despite extensive studies on upstream stimuli that activate AMPK, investigation on the downstream substrate(s) of AMPK-mediated glucose uptake is lacking. More recent reports revealed that Akt substrate of 160 kDa (AS160) is an important substrate downstream of Akt that is involved in insulin-stimulated glucose uptake. In addition to insulin, contraction and activation of AMPK by AICAR is associated with increased phosphorylation of AS160 in rodent skeletal muscle. Phosphorylation of AS160 is impaired or abolished in skeletal muscle from AMPK a2 knockout, g3 knockout, and a2-kinase dead mice in response to AICAR treatment. This corroborates findings of impaired AICAR-stimulated glucose uptake in skeletal muscle of such mice. Therefore, AS160 appears to be a downstream target of AMPK in mediating glucose uptake in skeletal muscle.

Taken together, all these metabolic effects evidence that AMPK suppresses liver gluconeogenesis and lipid production, while decreasing hepatic lipid deposition via increased lipid oxidation, thus improving the glucose and lipid profiles in T2D.

More recently, involvement of AMPK in the regulation of not only cellular but also whole body energy metabolism has become apparent. It was shown that the adipocyte-derived hormone leptin leads to a stimulation of AMPK and therefore to an increase in fatty acid oxidation in skeletal muscle. Adiponectin, another adipocyte derived hormone leading to improved carbohydrate and lipid metabolism, has been shown to stimulate AMPK liver and skeletal muscles. The activation of AMPK in these circumstances seems independent of increasing cellular AMP levels but rather due to phosphorylation by one or more upstream kinases yet to be identified.

Based on the knowledge of the above-mentioned consequences of AMPK activation, deep beneficial effects would be expected from in vivo activation of AMPK. In liver, decreased expression of gluconeogenic enzymes would be expected to reduce hepatic glucose output and improve overall glucose homeostasis; both direct inhibition and/or reduced expression of key enzymes in lipid metabolism would be expected to increase glucose uptake and fatty acid oxidation with resulting improvement of glucose homeostasis and, due to a reduction in intra-myocyte triglyceride accumulation, to improved insulin action. Finally, the increase in energy expenditure should lead to a decrease in body weight. The combination of these effects in the metabolic syndrome would be expected to significantly reduce the risk of developing cardiovascular diseases. Several studies in rodents support this hypothesis. Until recently, most in vivo studies relied on AICAR AMPK activator, a cell permeable precursor of ZMP. ZMP, a structural analogue of AMP, acts as an intracellular AMP mimic and, when accumulated to high enough levels, is able to stimulate AMPK activity. However, ZMP also acts as an AMP mimic in the regulation of other enzymes, and is therefore not a specific AMPK activator. Several in vivo studies have demonstrated beneficial effects of both acute and chronic AICAR administrations in rodent models of obesity and type 2 diabetes. For example, 7 week AICAR administration in the obese Zucker (fa/fa) rat leads to a reduction in plasma triglycerides and free fatty acids, an increase in HDL cholesterol, and a normalisation of glucose metabolism as assessed by an oral glucose tolerance test (Minokoshi Y. et al. "Leptin stimulates fatty-acid oxidation by activating AMP-activated protein kinase", Nature, 415, 339, 2002)). In both ob/ob and db/db mice, 8 day AICAR administration reduces blood glucose by 35% (Halseth A. E. et al. "Acute and chronic treatment of ob/ob and db/db mice with AICAR decreases blood glucose concentrations", Biochem. Biophys. Res.

Comm., 294, 798 (2002)). In addition to AICAR, it was found that the diabetes drug metformin can activate AMPK in vivo at high concentrations, although it has to be determined to what extent its antidiabetic action relies on this activation. As with leptin and adiponectin, the stimulatory effect of metformin is indirect via activation of an upstream kinase. More recently, a small molecule AMPK activator has been described. This direct AMPK activator, named A-769662, is a thienopyridone and induces in vivo a decrease in plasma levels of glucose and triglycerides.

In addition to pharmacological intervention, several transgenic mice models have been developed in the last years, and initial results are currently becoming available. Expression of dominant negative AMPK in skeletal muscle of transgenic mice demonstrated the effect of AICAR on stimulation of glucose transport is dependent on AMPK activation, and therefore likely not caused by non-specific ZMP effects. Similar studies in other tissues will help to further define the consequences of AMPK activation. It is expected that pharmacological activation of AMPK will have benefits in the metabolic syndrome with improved glucose and lipid metabolisms and reduction in body weight. In order to qualify a patient as having metabolic syndrome, three out of the five following criteria must be met:

1) elevated blood pressure (above 130/85 mmHg),
2) fasting blood glucose above 110 mg/dl,
3) abdominal obesity above 40" (men) or 35" (women) waist circumference, and blood lipid changes as defined by
4) increase in triglycerides above 150 mg/dl or
5) decrease in HDL cholesterol below 40 mg/dl (men) or 50 mg/dl (women).

Therefore, the combined effects that may be achieved through activation of AMPK in a patient who is qualified as having metabolic syndrome would raise the interest of this target.

Stimulation of AMPK has been shown to stimulate expression of uncoupling protein 3 (UCP3) skeletal muscle and might therefore be a way to prevent from damage from reactive oxygen species. Endothelial NO synthase (eNOS) has been shown to be activated through AMPK mediated phosphorylation, therefore AMPK activation can be used to improve local circulatory systems.

AMPK has a role in regulating the mTOR pathway. mTOR is a serine/threonine kinase and is a key regulator of protein synthesis. To inhibit cell growth and protect cells from apoptosis induced by glucose starvation, AMPK phosphorylates TSC2 at Thr-1227 and Ser-1345, increasing the activity of the TSC1 and TSC-2 complexes to inhibit m-TOR. In addition, AMPK inhibits mTOR action by phosphorylation on Thr-2446. Thus, AMPK indirectly and directly inhibits the activity of mTOR to limit protein synthesis. AMPK may also be a therapeutic target for many cancers that have constitutive activation of the PI3K-Akt signaling pathway. Treatment of various cancer cell lines by AICAR attenuated the cell proliferation both in in vitro and in vivo studies. Two reports link the treatment with metformin with a lower risk of cancer in diabetic patients.

Activation of AMPK by AICAR has been shown to reduce expression of the lipogenic enzymes FAS and ACC, resulting in suppression of proliferation in prostate cancer cells. Many cancer cells display a markedly increased rate of de novo fatty acid synthesis correlated with high levels of FAS. Inhibition of FAS suppresses cancer cell proliferation and induces cell death. Thus, AMPK activation and inhibition of FAS activity is a clear target for pharmacological therapy of cancers.

In some publications it has been described that AICAR as an AMPK activator exerts anti-inflammatory effects. It has been observed that AICAR attenuates the production of proinflammatory cytokines and mediators, AICAR in rat model and in vitro attenuates EAE progression by limiting infiltration of leucocytes across blood brain barrier (BBB) and it has been suggested recently that AMPK activating agents act as anti-inflammatory agents and can hold a therapeutic potential in Krabbe disease/twitcher disease (an inherited neurological disorder).

PRIOR ART

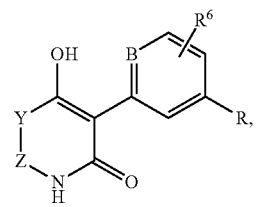

U.S. Pat. No. 5,602,144 discloses thienopyridone derivatives of the formula wherein B is CH or N, and

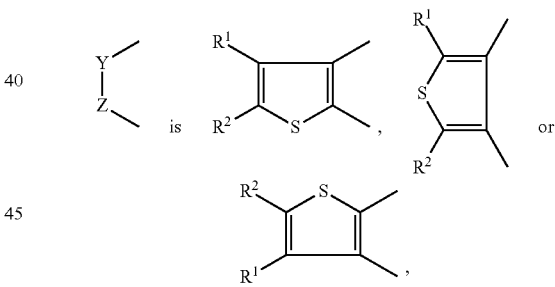

for the treatment of cerebral ischemia or schizophrenia.

U.S. Pat. No. 7,119,205 discloses thienopyridones derivatives of the formula

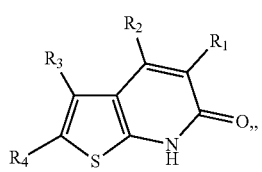

wherein $R_1$ is neither a aryl nor a heteroaryl group, useful for the treatment of diabetes, obesity as AMPK activators.

WO2007/019914 discloses thienopyridones derivatives of the formula

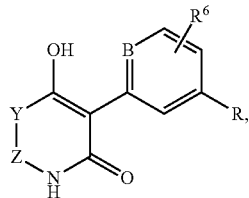

wherein B is CH or N and

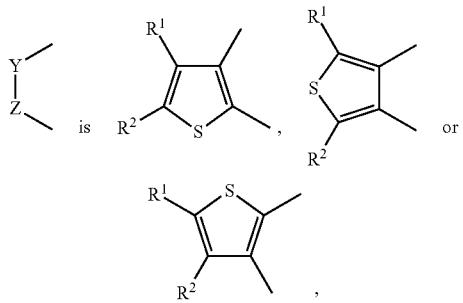

useful for the treatment of diabetes, obesity as AMPK activators.

WO2009/124636 discloses thienopyridones derivatives of the formula

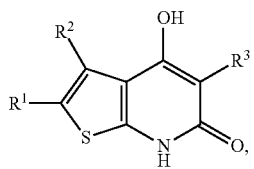

wherein $R^2$ is an aryl or heteroaryl group, useful for the treatment of diabetes, obesity as AMPK activators.

WO2009/135580 discloses thienopyridones derivatives of the formula

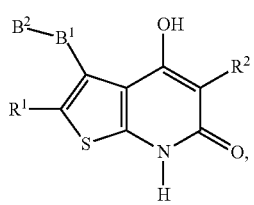

wherein $B^1$ and $B^2$ are aryl or heteroaryl groups, useful for the treatment of diabetes, obesity as AMPK activators.

DESCRIPTION OF THE INVENTION

The present invention discloses compounds of formula (1):

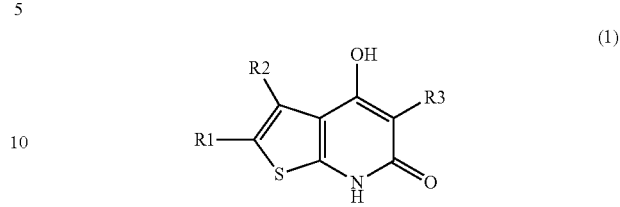

(1)

wherein

R1 represents a hydrogen atom or a halogen atom;

R2 represents an indanyl or tetralinyl group, substituted or not by one or more (e.g. 2, 3, 4, 5, 6 or 7) groups selected from halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

R3 represents an aryl or heteroaryl group, substituted or not by one or more (e.g. 2, 3, 4 or 5) atoms or groups selected from halogen atoms, alkyl groups, hydroxy, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

Compounds of formula (1) also include their geometric isomers, tautomers, epimers, enantiomers, stereoisomers, diastereoisomers, racemates, pharmaceutically acceptable salts, prodrugs, solvates, and mixtures thereof in all ratios.

Compounds of formula (1) are direct AMPK activators.

Compounds of formula (1) are useful for the treatment of diseases for which AMPK activation has a positive effect onto subject health. Among diseases for which treatment with compounds of formula (1) is suitable may be cited diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies.

In accordance with the present invention and as used herein, the following terms are defined with the following meanings unless explicitly stated otherwise.

The term "alkyl group" refers to a linear or branched saturated chain of 1 to 5 carbon atoms, such as methyl, ethyl, n-propyl, iso-propyl, n-butyl, sec-butyl, iso-butyl or tert-butyl. Preferably, alkyl groups are linear or branched saturated chains of 1 to 3 carbon atoms, such as methyl, ethyl, n-propyl or iso-propyl groups.

The term "aryl group" refers to a C6-C18 aromatic group, such as phenyl or naphthyl group, optionally substituted by one or more atoms or groups selected from halogen atoms, alkyl groups, hydroxy (OH), alkyloxy groups, amino ($NH_2$), mono- or di-alkylamino groups, carboxy (COOH), alkyloxycarbonyl groups, mono- or di-alkylaminocarbonyl groups, carboxamide ($CONH_2$), cyano (CN), alkylsulfonyl groups and trifluoromethyl ($CF_3$). More specifically, the aryl group can be substituted or not by fluorine, chlorine, bromine atoms, hydroxy, methoxy, ethoxy, amino, dimethylamino, diethylamino, methyl, ethyl, n-propyl, n-butyl, iso-propyl, sec-butyl, iso-butyl, tert-butyl, carboxy, methoxycarbonyl, ethoxycarbonyl, carboxamide, dimethylaminocarbonyl, methylaminocarbonyl, cyano, methylsulfonyl, or trifluoromethyl group.

The term "alkyloxy" (or "alkoxy") group refers to an alkyl group as defined above linked to the rest of the molecule through an oxygen atom. Among alkyloxy groups can be more specifically cited methoxy and ethoxy groups.

The term "alkylamino group" refers to an alkyl group as defined above linked to the rest of the molecule through a nitrogen atom. Among alkylamino groups can be cited dimethylamino and diethylamino groups.

The term "alkyloxycarbonyl group" refers to an alkyloxy group as defined above linked to the rest of the molecule through a carbonyl group.

The term "alkylaminocarbonyl group" refers to an alkylamino group as defined above linked to the rest of the molecule through a carbonyl group.

The term "alkylsulfonyl" refers to an alkyl as defined above linked to the rest of the molecule through a SO2 group. Among alkylsulfonyl groups can be cited methylsulfonyl and ethylsulfonyl groups.

The term "halogen atom" refers to an atom selected from fluorine, chlorine, bromine and iodine atoms.

The term "heteroaryl group" refers to a C5-C18 aromatic group including one or more heteroatoms selected from nitrogen, oxygen and sulphur. Among heteroaryl groups can be cited pyridine, pyrazine, pyrimidine, thiophene, furan, isoxazole, isothiazole, pyrazole, imidazole. Such groups may be substituted by atoms or groups selected from halogen atoms, alkyl groups, hydroxy (OH), alkyloxy groups, amino ($NH_2$), mono- or di-alkylamino groups, carboxy (COOH), alkyloxycarbonyl groups, mono- or di-alkylaminocarbonyl groups, carboxamide ($CONH_2$), cyano (CN), alkylsulfonyl groups and trifluoromethyl ($CF_3$). More specifically, the heteroaryl group can be substituted or not by fluorine, chlorine, bromine atoms, hydroxy, methoxy, ethoxy, amino, dimethylamino, diethylamino, methyl, ethyl, n-propyl, n-butyl, iso-propyl, sec-butyl, iso-butyl, tert-butyl, carboxy, methoxycarbonyl, ethoxycarbonyl, carboxamide, dimethylaminocarbonyl, methylaminocarbonyl, cyano, methylsulfonyl, or trifluoromethyl group.

"Solvates" of the compounds are taken in the present invention to mean adductions of inert solvent molecules onto the compounds which form owing to their mutual attractive force. Solvates are, for example, mono- or dihydrates or alcoholates.

A particular object of the present invention is a compound of formula (1), wherein R1 represents a halogen atom, in particular a chlorine atom.

Another particular object of the present invention is a compound of formula (1), wherein R2 represents a tetralinyl group substituted or not by one or more (e.g. 2, 3, 4, 5, 6 or 7) groups selected from halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

Another particular object of the present invention is a compound of formula (1), wherein R2 represents an indanyl group substituted or not by one or more (e.g. 2, 3, 4, 5 or 6) groups selected from halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

In a particular embodiment, the present invention is a compound of formula (1), wherein R2 represents an indanyl or tetralinyl group substituted by 1 or 2 substituents.

In a particular embodiment, the present invention is a compound of formula (1), wherein R2 represents an indanyl or tetralinyl group unsubstituted or substituted by a hydroxy group.

According to a specific embodiment, the compound of the invention is of formula (1) wherein R3 represents an aryl group.

Another particular object of the present invention is a compound of formula (1), wherein R3 represents a phenyl group, substituted or not by one or more (e.g. 2, 3, 4 or 5) atoms or groups selected from halogen atoms, alkyl groups, hydroxy, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

Another particular object of the present invention is a compound of formula (1), wherein R3 represents a pyridyl group, substituted or not by one or more (e.g. 2, 3 or 4) atoms or groups selected from halogen atoms, alkyl groups, hydroxy, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

In a particular embodiment, the present invention is a compound of formula (1), wherein R3 represents an aryl or heteroaryl group substituted by 1 or 2 substituents, preferably 1 substituent.

In a particular embodiment, the present invention is a compound of formula (1), wherein R3 represents an aryl or heteroaryl group, preferably a phenyl or pyridyl group, unsubstituted or substituted by one or more (e.g. 2, 3, or 4) atoms or groups selected from halogen atom, an alkyl, alkoxy and a cyano group.

Another particular object of the present invention is a compound of formula (1), wherein the compound of formula (1) is in the form of a salt, preferably a sodium or potassium salt. In particular, the compound of formula (1) is in the form of a mono-, di- or tri-sodium or potassium salt.

Any combination (whenever possible) of the above described particular embodiments corresponds to preferred embodiments of the inventive compounds.

The invention additionally relates to crystalline and polymorphic forms of compounds of formula (1) and derivatives described above.

The present invention is directed not only to racemic mixtures of these compounds, but also to individual stereoisomers and/or diastereoisomers thereof as well or as mixtures of these in all proportions.

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s). This also includes biodegradable polymer derivatives of the compounds according to the invention, as is described, for example, in Int. J. Pharm. 115, 61-67 (1995).

Some preferred compounds of formula (1) are the following:
2-chloro-4-hydroxy-3-indan-5-yl-5-phenyl-7H-thieno[2,3-b]pyridin-6-one
2-chloro-5-(4-fluorophenyl)-4-hydroxy-3-indan-5-yl-7H-thieno[2,3-b]pyridin-6-one
2-chloro-4-hydroxy-3-indan-5-yl-5-(3-methoxyphenyl)-7H-thieno[2,3-b]pyridin-6-one 2-chloro-4-hydroxy-3-indan-5-yl-5-(4-methoxyphenyl)-7H-thieno[2,3-b]pyridin-6-one
3-(2-chloro-4-hydroxy-3-indan-5-yl-6-oxo-7H-thieno[2,3-b]pyridin-5-yl)benzonitrile
2-chloro-4-hydroxy-3-indan-5-yl-5-(3-methylphenyl)-7H-thieno[2,3-b]pyridin-6-one
2-chloro-5-(4-fluorophenyl)-4-hydroxy-3-(4-hydroxyindan-5-yl)-7H-thieno[2,3-b]pyridin-6-one
2-chloro-5-(3-fluorophenyl)-4-hydroxy-3-(4-hydroxyindan-5-yl)-7H-thieno[2,3-b]pyridin-6-one
2-chloro-4-hydroxy-3-indan-5-yl-5-(3-pyridyl)-7H-thieno[2,3-b]pyridin-6-one
2-chloro-4-hydroxy-3-(4-hydroxyindan-5-yl)-5-phenyl-7H-thieno[2,3-b]pyridin-6-one
2-chloro-5-(2-fluorophenyl)-4-hydroxy-3-(4-hydroxyindan-5-yl)-7H-thieno[2,3-b]pyridin-6-one
2-chloro-4-hydroxy-3-(5-hydroxytetralin-6-yl)-5-phenyl-7H-thieno[2,3-b]pyridin-6-one
3-(2-chloro-4-hydroxy-6-oxo-3-tetralin-6-yl-7H-thieno[2,3-b]pyridin-5-yl)benzonitrile
2-chloro-4-hydroxy-5-(3-pyridyl)-3-tetralin-6-yl-7H-thieno[2,3-b]pyridin-6-one
Trisodium 2-chloro-3-(5-oxidotetralin-6-yl)-5-phenyl-thieno[2,3-b]pyridine-4,6-diolate
2-chloro-4-hydroxy-5-phenyl-3-tetralin-6-yl-7H-thieno[2,3-b]pyridin-6-one
2-chloro-5-(4-fluorophenyl)-4-hydroxy-3-(5-hydroxytetralin-6-yl)-7H-thieno[2,3-b]pyridin-6-one
disodium 2-chloro-3-(5-oxidotetralin-6-yl)-6-oxo-5-phenyl-7H-thieno[2,3-b]pyridin-4-olate
2-chloro-4-hydroxy-3-(5-hydroxytetralin-6-yl)-5-(3-methylphenyl)-7H-thieno[2,3-b]pyridin-6-one
2-chloro-4-hydroxy-3-(5-hydroxytetralin-6-yl)-5-(4-methylphenyl)-7H-thieno[2,3-b]pyridin-6-one
2-chloro-5-(3-fluorophenyl)-4-hydroxy-3-(5-hydroxytetralin-6-yl)-7H-thieno[2,3-b]pyridin-6-one
sodium 2-chloro-3-(5-hydroxytetralin-6-yl)-6-oxo-5-phenyl-7H-thieno[2,3-b]pyridin-4-olate
potassium 2-chloro-3-(5-hydroxytetralin-6-yl)-6-oxo-5-phenyl-7H-thieno[2,3-b]pyridin-4-olate Preparation of Compounds of Formula (1)

The compounds of the present invention may be prepared in a number of methods well known to those skilled in the art, including, but not limited to, those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, potassium tertiobutylate, sodium tertioamylate, triethylamine, potassium hexamethyldisilazide, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether, dioxane and tetrahydrofuran.

The reactions can take place over a wide range of temperatures. In general, we find it convenient to carry out the reaction at a temperature of from 0° C. to 150° C. (more preferably from about room temperature to 100° C.). The time repaired for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

Compounds of formula (1) could be obtained from compounds of formula (2)

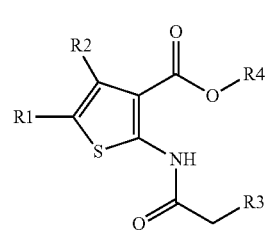

(2)

wherein R1, R2 and R3 have the meaning previously described
wherein R4 is methyl or ethyl and a base such as, but not limited to, potassium hexamethyldisilazide or sodium hydride. Compounds of formula (2) could be obtained from the reaction between compounds of formula (3) and compounds of formula (4):

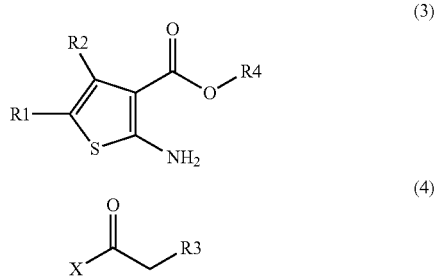

wherein R1, R2, R3 and R4 have the meaning previously described wherein X is OH or a halogen atom (such as Cl or Br).

When X is OH, a carbodiimide coupling agent is needed, such as but not limited to HBTU (see the following internet link for in depth description: http://chemicalland21.com/life-science/phar/HBTU.htm).

Compounds of formula (3) are easily prepared by a person skilled in the Art by a Gewald reaction described in Journal Heterocycle Chemistry, vol. 36, page 333, 1999.

Pharmaceutical Salts and Other Forms

The compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of formula (1) are for most prepared by conventional methods. If the compound of formula (1) contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of formula (1) are likewise included. In the case of some compounds of formula (1), acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of formula (1) include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula (1) which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl $(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula (1) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of compounds of formula (1) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salts forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of formula (1) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of formula (1) according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

For chiral resolution of the racemates, the following acids and amines can be used: As examples, the following chiral acids can be used: (+)-D-di-O-benzoyltartaric acid, (−)-L-di-O-benzoyltartaric acid, (−)-L-di-O,O'-p-toluyl-L-tartaric acid, (+)-D-di-O,O'-p-toluyl-L-tartaric acid, (R)-(+)-malic acid, (S)-(−)-malic acid, (+)-camphoric acid, (−)-camphoric acid, R-(−)1,1'-binaphtalen-2,2'-diyl hydrogenophosphonic, (+)-camphanic acid, (−)-camphanic acid, (S)-(+)-2-phenylpropionic acid, (R)-(+)-2-phenylpropionic acid, D-(−)-mandelic acid, L-(+)-mandelic acid, D-tartaric acid, L-tartaric acid, or any mixture of them.

As examples, the following chiral amines can be used: quinine, brucine, (S)-1-(benzyloxymethyl)propylamine (III), (−)-ephedrine, (4S,5R)-(+)-1,2,2,3,4-tetramethyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)-phenylglycinol, (S)-α-methylbenzylamine or any mixture of them.

The present invention also relates to the compounds of the invention for use in a method of treatment of a subject, in particular of treatment of diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies.

In a preferred embodiment, the compounds of the invention are for use in a method of treatment of diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia or hypercholesterolemia.

The term "cancer" in the present invention includes cancers with solid or liquid tumors. In particular, it refers to glioblastomas, neuroblastomas, leukemias, prostate cancers, ovarian cancers, lung cancers, breast cancers, digestive cancers, in particular liver cancers, pancreatic cancers, head and neck cancers, colon cancers, lymphomas and melanomas.

The invention furthermore relates to a pharmaceutical composition comprising at least one compound according to the invention and a pharmaceutically acceptable support.

A further object of this invention is a method for treating diseases regulated by activation of AMPK, more specifically diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies, the method comprising administering to a subject in need thereof an effective amount of a compound of the invention.

The invention furthermore relates to the use of compounds of the invention for the preparation of a pharmaceutical composition, in particular for the treatment of diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies.

The pharmaceutical composition according to the invention may be prepared by any conventional method. Compounds of the invention can be converted into a suitable dosage form here together with at least one solid, liquid and/or semi-liquid excipient or adjuvant and, if desired, in combination with one or more further active ingredients.

The term "pharmaceutically acceptable support" refers to carrier, adjuvant, or excipient acceptable to the subject from a pharmacological/toxicological point of view and to the manufacturing pharmaceutical chemist from a physical/chemical point of view regarding to composition, formulation, stability, subject acceptance and bioavailability.

The term "carrier", "adjuvant", or "excipient" refers to any substance, not itself a therapeutic agent, that is added to a pharmaceutical composition to be used as a carrier, adjuvant, and/or diluent for the delivery of a therapeutic agent to a subject in order to improve its handling or storage properties or to permit or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc.

The term "treatment" or "treating" refers to therapy, prevention and prophylaxis of a disorder which can be potentially regulated by activation of AMPK, in particular diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies.

The treatment involves the administration of a compound or pharmaceutical composition to a subject having a declared disorder to cure, delay, or slow down the progress, thus improving the condition of patients. The treatment may be also administered to healthy subjects that are at risk of developing a disorder, in particular diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies.

Within the context of the invention, the term "subject" means a mammal and more particularly a human. The subjects to be treated according to the invention can be appropriately selected on the basis of several criteria associated to the disease such as previous drug treatments, associated pathologies, genotype, exposure to risk factors, viral infection, as well as any other relevant biomarker that can be evaluated by means of immunological, biochemical, enzymatic, chemical, or nucleic acid detection method. In a particular embodiment, the subject is an overweighed patient (in particular an overweighed prediabetic patient) or obese patient suffering from atherogenic dyslipidemia. Indeed, these patients are at risk of developing a disease which can be potentially regulated by activation of AMPK, in particular diabetes, metabolic syndrome, obesity, liver disease, hepatic steatosis, non alcoholic fatty liver disease (NAFLD), non alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies.

Pharmaceutical compositions can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical compositions can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical compositions of this type can be prepared using a process which is generally known in the pharmaceutical art.

The ratio between the compounds of the invention and the pharmaceutically acceptable support may be comprised in a wide range. In particular, this ratio may be comprised between 5/95 (w/w) and 95/5 (w/w), preferably between 10/90 (w/w) and 90/10 (w/w), in particular between 10/90 (w/w) and 50/50 (w/w).

Pharmaceutical compositions can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such compositions can be prepared using all processes known in the pharmaceutical art by, for example, combining the active ingredient with the excipient(s) or adjuvant(s).

Pharmaceutical compositions adapted for oral administration can be administered as separate units, such as, for example, capsules or tablets; powders or granules; solutions or suspensions in aqueous or non-aqueous liquids; edible foams or foam foods; or emulsions, such as oil-in-water liquid emulsions or water-in-oil liquid emulsions.

Thus, for example, in the case of oral administration in the form of a tablet or capsule, the active ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compounds. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention can also be delivered using monoclonal antibodies as individual carriers to which the compound molecules are coupled. The compounds can also be coupled to soluble polymers as targeted medicament carriers.

Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical compositions adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compositions adapted for topical administration can be formulated as ointments, creams, suspensions, lotions, powders, solutions, pastes, gels, sprays, aerosols or oils.

For the treatment of the eye or other external tissue, for example mouth and skin, the compositions are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical compositions adapted for topical application to the eye include eye drops, in which the active ingredient is dissolved or suspended in a suitable carrier, in particular an aqueous solvent.

Pharmaceutical compositions adapted for topical application in the mouth encompass lozenges, pastilles and mouthwashes.

Pharmaceutical compositions adapted for rectal administration can be administered in the form of suppositories or enemas.

Pharmaceutical compositions adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical compositions adapted for administration by inhalation encompass finely particulate dusts or mists, which can be generated by various types of pressurised dispensers with aerosols, nebulisers or insufflators.

Pharmaceutical compositions adapted for vaginal administration can be administered as pessaries, tampons, creams, gels, pastes, foams or spray formulations.

Pharmaceutical compositions adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the compositions may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise disease condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The following examples illustrate the invention without, however, limiting it. The starting materials used are known products or products prepared according to known procedures. The percentages are expressed on a weight basis, unless otherwise mentioned.

EXAMPLES

The compounds were characterised especially via the following analytical techniques:
NMR spectra were acquired using a Bruker Avance DPX 300 MHz NMR spectrometer;
masses (MS) were determined by HPLC coupled to an Agilent Series 1100 mass detector.

Example 1

2-chloro-4-hydroxy-3-indan-5-yl-5-(4-methoxyphenyl)-7H-thieno[2,3-b]pyridin-6-one Step 1: 1-(indan-5-yl)ethanone (10 g, 62.4 mmol) was dissolved in toluene (200 mL) followed by acetic acid (3.57 mL, 62.4 mmol), ammonium acetate (12.03 g, 156 mmol) and ethyl 2-cyanoacetate (160 mL, 1503 mmol). The reaction mixture was boiled for 10 h. Upon cooling, water was added and ethyl acetate extraction was performed (3×200 mL). Organic phases were combined and washed with brine, dried over sodium sulfate. After removal of the solvent, the crude product was purified over silica (heptane/ethyl acetate 60/40) affording 13 g (44%) of an oil.
LC/MS: purity 54%, M−1=254

Step 2: step 1 compound (10.4 g, 22 mmol) was dissolved in ethanol (100 mL). Morpholine (2.3 mL, 26.4 mmol) and sulphur (1.7 g, 6.6 mmol) were added to the reaction mixture and the whole was refluxed for 20 h. Upon cooling, the reaction mixture was filtered and the solids rinsed with water. The aqueous layer was extracted with ether, washed with brine and dried over sodium sulfate. Removal of the solvent afforded 4.3 g (68%) of a brown oil.
NMR $^1$H (DMSO-d6): 0.95 (t, 3H); 2.03 (m, 2H); 2.86 (m, 4H); 2.97 (q, 2H); 6.12 (s, 1H); 6.99 (d, 1H); 7.10 (s, 1H); 7.15 (dd, 1H); 7.36 (bs, 2H)

Step 3: step 2 compound (8.98 g, 31.2 mmol) was dissolved in $CH_2Cl_2$ (200 mL). N-chlorosuccinimide (4.17 g, 31.2 mmol) was slowly added and the reaction was stirred at 20° C. for 1 hour. Water was added. The aqueous layer was extracted with ethyl acetate (3×100 ml) and the combined organic layers were washed with brine and dried over sodium sulfate. After removal of the solvent, the crude product was purified over silica (heptane/AcOEt 95/5) affording 5.9 g (47%) of expected product.
LC/MS: purity 80%, M+1=322

Step 4: To step 3 compound (1.6 g, 4.3 mmol) and potassium carbonate (893 mg, 6.5 mmol) in tetrahydrofuran (20 mL) was added 4-methoxyphenyl acetyl chloride (0.66 ml, 4.3 mmol). The reaction mixture was stirred 18 h at 20° C. Water was added and ether extraction (3×100 mL) was performed. The combined organic layers were washed with brine and dried over sodium sulfate. After removal of the solvent, the crude product was purified over silica (heptane/ether 80/20) affording 886 mg (43.9%) of the expected product.
LC/MS: purity 98.1%, M−1=468.0

Step 5: To potassium bis(trimethylsilyl)amide (1.50 g, 7.5 mmol in THF (20 mL)) was added step 4 compound (884 mg, 1.9 mmol) and the reaction mixture was stirred 30 minutes at 10° C. The reaction mixture was poured in a mixture of HCl 1N/ice, and extracted with ethylacetate (3×100 mL). The combined organic layers were washed with brine and dried over sodium sulfate. After removal of the solvent, the crude solid was poured into a mixture of heptane/ether. After filtration, 77 mg (6%) of the expected compound was obtained.
LC: RT 5.49 min, purity 93.1%
MS: M−1=422
NMR $^1$H (DMSO-d6): 2.02 (m, 2H); 2.87 (m, 4H); 3.74 (s, 3H); 6.88 (dd, 2H); 7.09 (dd, 1H); 7.12 (dd, 2H); 7.19-7.24 (m, 3H); 9.28 (bs, 1H)

Example 2

2-chloro-4-hydroxy-3-(4-hydroxyindan-5-yl)-5-phenyl-7H-thieno[2,3-b]pyridin-6-one Step 1: 2,3-dihydro-1H-inden-4-ol (9.9 g, 73.8 mmol) was dissolved in acetic anhydride (13.92 ml, 148 mmol) and the reaction mixture was refluxed for 3 h. Upon cooling, the solvent was removed under reduced pressure affording 12 g (92%) of an oil.
NMR $^1$H (DMSO-d6): 2.00 (m, 2H); 2.27 (s, 3H); 2.70 (dd, 2H); 2.91 (dd, 2H); 6.87 (d, 1H); 7.11-7.19 (m, 2H)

Step 2: step 1 compound (12 g, 68.1 mmol) and aluminium chloride (10 g, 74.9 mmol) were added to 1,2-Dichlorobenzene (70 mL). The reaction mixture was heated 18 hours at 100° C. The mixture was poured on ice/water/HCl 3N aid extracted with chloroform (3×200 mL). Combined organic layers were dried over sodium sulfate. After removal of the solvent, the crude product was purified over silica (cyclohexane then dichloromethane) affording 7.3 g (61%) of colorless oil.
LC/MS: purity 99%, M+1=177

Step 3: step 2 compound (7.3 g, 41.4 mmol), iodomethane (5.18 mL, 83 mmol), and cesium carbonate (16.20 g, 49.7 mmol) were added to acetone (40 mL). The reaction mixture was stirred overnight at room temperature. Water was added and ethyl acetate (3×100 mL) extraction was performed. Combined organic layers were dried over sodium sulfate. After removal of the solvent, the crude product was purified over silica (dichloromethane) affording 7.3 g (94%) of a colorless oil.
NMR $^1$H (DMSO-d6): 2.10 (m, 2H); 2.50 (m, 3H); 2.85 (dd, 2H); 2.95 (dd, 2H); 3.80 (s, 3H); 7.10 (d, 1H); 7.40 (d, 1H)

Step 4: step 3 compound (7.3 g, 38.4 mmol) and ethyl 2-cyanoacetate (6.14 mL, 57.6 mmol) were added to acetic acid (60 mL). Hexamethyldisilazane was added slowly and the reaction mixture was heated at 50° C. overnight. Upon cooling, water was added and the reaction mixture was extracted with ethylacetate (3×100 mL). Combined organic layers were washed twice with brine and dried over sodium sulfate. After removal of the solvent, 11.1 g (98%) of brown oil were obtained.

LC/MS: purity 97%, M−1=270

Step 5: step 4 compound (10.9 g, 38.2 mmol), sulfur (3.06 g, 96 mmol), and morpholine (4.01 mL, 45.8 mmol) were added to ethanol (160 mL). The reaction mixture was refluxed 7 h. Upon cooling, the reaction mixture was filtered and the solvent removed under reduced pressure. The crude product was purified over silica (Heptane/ethylacetate 95/5) affording 7.4 g (61%) of a brown oil.

LC/MS: purity 99%, M+1=318

Step 6: step 5 compound (7.32 g, 22.83 mmol) was dissolved in chloroform (70 mL) and N-chlorosuccinimide (3.11 g, 22.83 mmol) was added. After 1 h at −5° C., the reaction mixture was washed with water and dried over sodium sulfate. After removal of the solvent, the crude product was purified over silica (Heptane/AcOEt 90/10 to 85:15) affording 7.22 g (89%) of an orange solid.

LC/MS: purity 99%, M−1=350

Step 7: step 6 compound (500 mg, 1.41 mmol) was dissolved in tetrahydrofuran (10 mL). Cesium carbonate (917 mg, 2.81 mmol) and phenylacetylchloride (0.23 mL, 1.69 mmol) were added and the reaction mixture was stirred 20 h at room temperature. Water was added and ethylacetate (2×15 mL) extraction was performed. Combined organic layers were washed with brine and dried over sodium sulfate. After removal of the solvent, 629 mg (93%) of a yellow oil were obtained.

LC/MS: purity 98%, M−1=468

Step 8: To a solution of potassium bis(trimethylsilyl)amide (1102 mg, 5.25 mmol) in tetrahydrofuran (5 mL) was added a solution of step 7 compound (629 mg, 1.31 mmol) in tetrahydrofuran (5 mL). The reaction mixture was stirred 30 minutes at 20° C. A mixture of water (15 mL) and acetic acid (5 mL) was added and the reaction mixture was extracted with ethylacetate (3×15 mL). Combined organic layers were washed with brine and dried over sodium sulfate. After removal of the solvent, the crude product was purified over silica (heptanes/ethyl acetate 60/40) affording 323 mg (56%) of a red solid.

LC/MS: purity 95.5%, M+1=424

Step 9: Methionine (324 mg, 2.17 mmol) was dissolved in methanesulfonic acid and step 8 compound (323 mg, 0.72 mmol) was added. The reaction mixture was stirred 20 h at 20° C. The reaction mixture was poured dropwise on bed water. Extraction with ethylacetate (3×10 mL) was performed. Combined organic layers were washed with brine and dried over sodium sulfate. After removal of the solvent, the crude product was purified over silica (heptane/ethyl acetate 50/50) affording 137 mg of a solid. This one was boiled in water affording 53 mg (18%) of a light brown solid.

LC: RT=4.73; purity 99%

MS: M+1=410.2

NMR $^1$H (DMSO-d6): 1.99 (m, 2H); 2.80 (m, 4H); 6.72 (dd, 1H); 6.89 (dd, 1H); 7.18-7.34 (m, 5H); 8.59 (bs, 1H); 9.14 (bs, 1H); 11.54 (bs, 1H)

The following compounds in Table (1) can be obtained analogously.

| No | name | MS |
| --- | --- | --- |
| 3 | 2-chloro-4-hydroxy-3-indan-5-yl-5-phenyl-7H-thieno[2,3-b]pyridin-6-one | 392 (M − 1) |
| 4 | 2-chloro-5-(4-fluorophenyl)-4-hydroxy-3-indan-5-yl-7H-thieno[2,3-b]pyridin-6-one | 410 (M − 1) |
| 5 | 2-chloro-4-hydroxy-3-indan-5-yl-5-(3-methoxyphenyl)-7H-thieno[2,3-b]pyridin-6-one | 422 (M − 1) |
| 6 | 3-(2-chloro-4-hydroxy-3-indan-5-yl-6-oxo-7H-thieno[2,3-b]pyridin-5-yl)benzonitrile | 417 (M − 1) |
| 7 | 2-chloro-4-hydroxy-3-indan-5-yl-5-(m-tolyl)-7H-thieno[2,3-b]pyridin-6-one | 406 (M − 1) |
| 8 | 2-chloro-5-(4-fluorophenyl)-4-hydroxy-3-(4-hydroxyindan-5-yl)-7H-thieno[2,3-b]pyridin-6-one | 428 (M + 1) |
| 9 | 2-chloro-5-(3-fluorophenyl)-4-hydroxy-3-(4-hydroxyindan-5-yl)-7H-thieno[2,3-b]pyridin-6-one | 428 (M + 1) |
| 10 | 2-chloro-4-hydroxy-3-indan-5-yl-5-(3-pyridyl)-7H-thieno[2,3-b]pyridin-6-one | 395 (M + 1) |
| 11 | 2-chloro-5-(2-fluorophenyl)-4-hydroxy-3-(4-hydroxyindan-5-yl)-7H-thieno[2,3-b]pyridin-6-one | 428 (M + 1) |

Example 12

2-chloro-4-hydroxy-3-(5-hydroxytetralin-6-yl)-5-phenyl-7H-thieno[2,3-b]pyridin-6-one Step 1: 5,6,7,8-tetrahydronaphthalen-1-ol (50.85 g, 340 mmol) was dissolved in acetic anhydride (500 ml) and triethylamine (56.8 ml, 408 mmol) was added to the reaction mixture. The whole was refluxed for 2 h. The reaction mixture was cooled to room temperature and the solvent was removed under reduced pressure. The crude remaining liquid was dissolved into ethyl acetate (500 mL) and the organic layer was washed several times with water and brine. The organic layer was then dried over Na$_2$SO4, filtered, concentrated under reduced pressure to give a dark oil (65.4 g; 91% yield)

LC: 4.94 min

Step 2: Aluminium chloride (45.1 g, 338 mmol) was dissolved in 1,2-dichlorobenzene (250 ml) then step 1 compound (65.4 g, 308 mmol) in 1,2-dichlorobenzene (250 ml) was added. The reaction mixture was heated at 100° C. for 17 h. The reaction mixture was cooled with an iced bath and HCl 6N (80 mL) was added dropwise. The mixture was filtered over celite. The organic solution was washed several times with water then dried on sodium sulfate and filtered. The solvent was removed under reduced pressure to give a dark oil. The oil was purified over silica (cyclohexane then cyclohexane/dichloromethane 1/1) to give a yellow solid (60 g; 91% yield)

LC/MS: purity 98%, M+1=191

Step 3: Step 2 compound (13.63 g, 70.2 mmol) was dissolved in acetone (200 ml) and cesium carbonate (23.11 g, 70.9 mmol) and iodomethane (4.41 ml, 70.9 mmol) were added to the reaction mixture. After 15 h of stirring at RT, additional iodomethane (0.2 eq) was added. 2 hours later, the reaction mixture was filtered over a pad of celite and the solvent removed under reduced pressure. The remaining oil was purified over silica (cyclohexane/AcOEt 95/5) producing a yellow oil (12.6 g; 84% yield)

LC/MS: purity 96%, M+1=205

Step 4: step 3 compound (12.56 g, 59.0 mmol) was dissolved in toluene (150 ml). Ethyl 2-cyanoacetate (7.56 ml, 70.8 mmol), ammonium acetate (7.74 g, 100 mmol) and acetic acid (2.70 ml, 47.2 mmol) were added to the reaction mixture. The whole was refluxed overnight. The solvent was removed under reduced pressure and the remaining crude oil dissolved in ethyl acetate (300 mL). The organic layer was washed with water and brine then dried over sodium sulfate, filtered and concentrated under reduced pressure to give an oil. This one was purified over silica (Heptane/ethyl acetate 95/5) delivering a green oil (14.7 g; 76% yield)

LC/MS: purity 91%, M+1=300

Step 5: step 4 compound (14.69 g, 49.1 mmol), morpholine (5.13 ml, 58.9 mmol), sulfur (3.78 g, 14.72 mmol) were mixed in ethanol (200 ml) and the whole was heated at 80° C. overnight. The reaction mixture was filtered over a pad of celite and the solvent removed under reduced pressure leaving a brown solid. This one was purified over silica (heptanes to heptanes/ethyl acetate 90/10 to heptanes/ethyl acetate 80/20). A yellow solid (12.4 g; 74% yield) was collected.

LC/MS: purity 97%, M+1=332

Step 6: step 5 compound (4.4 g, 13.28 mmol) was dissolved in chloroform (100 ml) and N-chlorosuccinimide (1.81 g, 13.28 mmol) was added, at −5° C., to the reaction mixture. The reaction mixture was then stirred 2 hours at 5° C. Ater that, the reaction mixture was washed with water, dried over sodium sulfate, filtered and the solvent removed under reduced pressure affording a purple oil. This oil was purified over silica (heptane/ethyl acetate 95/5 to 85/15). An orange oil (3.5 g; 70% yield) was recovered.

LC/MS: purity 97.5%, M+1=366

Step 7: step 6 compound (119 g, 325 mmol) and cesium carbonate (212 g, 650 mmol) were charged in THF (1600 ml) to give a red suspension. Phenylacetyl chloride (53.0 mL, 390 mmol) was added dropwise and the reaction mixture stirred at room temperature for 20 hours. The reaction mixture was poured onto water/ice and extracted with ethyl acetate. The organic phase was washed with sodium bicarbonate solution and brine. After removal of the solvent, the remaining crude oil was purified over silica (dichloromethane) affording a purple oil (153.1 g; 97% yield).

LC/MS: purity 99%, M+1=484

Step 8: Potassium bis(trimethylsilyl)amide (6.76 g, 33.9 mmol) was suspended in tetrahydrofuran (60 mL) and a solution of step 7 compound (4.1 g, 8.47 mmol) in tetrahydrofuran (20 mL) was added dropwise. After 30 minutes, the reaction mixture was was cooled to −5° C. and acetic acid (15 mL) was added dropwise. The reaction mixture was diluted with water (100 mL) and extracted with ethyl acetate. The organic phase was dried over sodium sulfate, filtered and concentred to dryness. The remaining crude oil was purified over silica (cyclohexane/ethyl actetate 70/30) affording a brown solid (2.05 g; 55% yield).

LC/MS: purity 99%, M+1=428

Step 9: step 8 compound (2.05 g, 4.63 mmol) was dissolved in methanesulfonic acid (30 mL) and methionine (2.074 g, 13.90 mmol) was added to the reaction mixture. After overnight stirring, the reaction mixture was poured onto water/ice. Extraction with ethyl acetate was performed and the organic phase was washed with water, sodium bicarbonate solution and brine. The organic solution was dried over sodium sulfate, filtered and brought to dryness. The crude remaining solid was purified over silica (cyclohexane/ethyl acetate 70/30) affording a off-white solid (1.67 g; 72% yield).

LC: 5.23 min; purity 99%

MS: M+1=424

NMR 1H (DMSO-d6): 1.77 (m, 4H); 2.63 (m, 2H); 2.74 (m, 2H); 6.63 (d, 1H); 6.90 (d, 1H); 7.24-7.41 (m, 5H); 8.24 (bs, 1H); 9.27 (bs, 1H); 11.62 (bs, 1H)

Example 13

2-chloro-4-hydroxy-5-(3-pyridyl)-3-tetralin-6-yl-7H-thieno[2,3-b]pyridin-6-one

Step 1: 1-(5,6,7,8-tetrahydronaphthalen-2-yl)ethanone (20 g, 115 mmol), ethyl 2-cyanoacetate (14.66 mL, 138 mmol), morpholine (20.08 mL, 230 mmol), and 14.72 g of sulfur were added to ethanol (115 mL) to give a yellow suspension. The reaction mixture was refluxed 20 h at 90° C. Upon cooling, the reaction mixture was filtered and the solvent removed under reduced pressure. The crude brown oil was dissolved in ethyl acetate, washed with HCl 1 N, brine twice and dried over sodium sulfate. After removal of the solvent, the crude was purified over silica (dichloromethane/cyclohexane 40/60) affording 9.6 g (28%) of a yellow oil.

LC/MS: purity 84%, M+1=302

Step 2: step 1 compound (9.2 g, 30.5 mmol) was dissolved in chloroform (400 mL). Upon cooling at −5° C., N-chlorosuccinimide (4.08 g) was added and the reaction mixture was stirred for 3 hours. The reaction mixture was purified over silica (heptane/ethyl acetate 80/20) affording 2.9 g (28%) of a brown oil.

NMR $^1$H (DMSO-d6): 0.75 (t, 3H); 1.75 (m, 4H); 2.50 (m, 4H); 3.80 (q, 2H); 6.70 (s, 1H); 6.80 (d, 1H); 7.00 (d, 1H)7.50 (bs, 1H)

Step 3: 3-(carboxymethyl)pyridinium chloride (538 mg, 3.10 mmol) and oxalyl dichloride (0.788 mL, 9.31 mmol) and a drop of dimethylformamide were dissolved in dichloromethane (3 mL). After 2 hours, solvent was removed and dimethylformamide (4 mL) was added, followed by potassium carbonate (1.28 g, 9.3 mmol) and step 2 compound (1.04 g, 3.10 mmol) in dimethylformamide (8 mL). The reaction mixture was stirred overnight and poured in iced water. An ethyl acetate extraction was performed and the organic layer was washed twice with brine and dried over sodium sulfate. A brown oil (1.25 g, 89%) was recovered after removal of the solvent.

LC/MS: purity 96%, M+1=455

Step 4: Potassium bis(trimethylsilyl)amide (2.2 g, 11 mmol) was dissolved in tetrahydrofuran (5 mL) and a solution of step 3 compound (1.25 g, 2.75 mmol) in tetrahydrofuran (9 mL) was added. After 30 minutes, a mixture of water/acetic acid was added (until pH 4) and an ethylacetate extraction was performed. The organic layer was washed twice with brine and dried over sodium sulfate. After removal of the solvent, a brown solid (0.62 g; 55%) was obtained.

LC: 4.15 min, purity 99%,

MS: M+1=409

NMR $^1$H (DMSO-d6): 1.76 (m, 4H); 2.74 (m, 4H); 7.06 (m, 3H); 7.34 (dd, 1H); 7.75 (d, 1H) 8.38 (d, 1H); 8.51 (s, 1H)

Example 14 sodium 2-chloro-3-(5-hydroxytetralin-6-yl)-6-oxo-5-phenyl-7H-thieno[2,3-b]pyridin-4-olate Step 1: 2-chloro-4-hydroxy-3-(5-hydroxytetralin-6-yl)-5-phenyl-7H-thieno[2,3-b]pyridin-6-one (4.0 g, 9.44 mmol) was dissolved in a mixture of methanol/tetrahydrofuran (25 ml/25 mL). Sodium methoxide solution (30% in methanol) (1.75 mL, 9.44 mmol) was slowly added followed by water (15 ml). Organic solvents were removed under reduced pressure. The remaining aqueous solution was lyophilized to give a grey solid (4.80 g, 100%, compound crystallized with 4 water molecules).

LC: 5.06 min, purity 99%,

MS: M+1=424

NMR $^1$H (DMSO-d6): 1.70 (m, 4H); 2.61 (m, 4H); 6.54 (d, 1H); 6.89 (d, 1H); 7.04 (dd, 1H); 7.18 (dd, 2H); 7.40 (d, 2H)

The following compounds in Table (2) can be obtained analogously.

| No | name | MS |
|---|---|---|
| 15 | 3-(2-chloro-4-hydroxy-6-oxo-3-tetralin-6-yl-7H-thieno[2,3-b]pyridin-5-yl)benzonitrile | 433 (M + 1) |
| 16 | trisodium 2-chloro-3-(5-oxidotetralin-6-yl)-5-phenyl-thieno[2,3-b]pyridine-4,6-diolate | 424 (M + 1) |
| 17 | 2-chloro-4-hydroxy-5-phenyl-3-tetralin-6-yl-7H-thieno [2,3-b]pyridin-6-one | 408 (M + 1) |
| 18 | 2-chloro-5-(4-fluorophenyl)-4-hydroxy-3-(5-hydroxytetralin-6-yl)-7H-thieno[2,3-b]pyridin-6-one | 442 (M + 1) |
| 19 | disodium 2-chloro-3-(5-oxidotetralin-6-yl)-6-oxo-5-phenyl-7H-thieno[2,3-b]pyridin-4-olate | 424 (M + 1) |
| 20 | 2-chloro-4-hydroxy-3-(5-hydroxytetralin-6-yl)-5-(m-tolyl)-7H-thieno[2,3-b]pyridin-6-one | 438 (M + 1) |
| 21 | 2-chloro-4-hydroxy-3-(5-hydroxytetralin-6-yl)-5-(p-tolyl)-7H-thieno[2,3-b]pyridin-6-one | 438 (M + 1) |
| 22 | 2-chloro-5-(3-fluorophenyl)-4-hydroxy-3-(5-hydroxytetralin-6-yl)-7H-thieno[2,3-b]pyridin-6-one | 442 (M + 1) |
| 23 | potassium 2-chloro-3-(5-hydroxytetralin-6-yl)-6-oxo-5-phenyl-7H-thieno[2,3-b]pyridin-4-olate | 424 (M + 1) |

Biological Assays
Enzymatic Activity

The following biological test allows the determination of the efficacy of compounds of formula (I) onto AMPK protein.

AMPK enzyme activities were assayed by using a Delfia technology. AMPK enzyme activities were carried out in microtiter plates in the presence of a synthetic peptide substrate (AMARAASAAALARRR, the "AMARA" peptide) and activators in serial dilutions. Reactions were initiated by the addition of AMPK. Enzyme activity was assayed by using an anti-phosphoserine antibody to measure the quantity of phosphate incorporated into the AMARAA.

N°: Number of the molecule

Activity: Ratio between the % of control (basal activity) of compound of formula (1) at 30 µM and the % of control (basal activity) of AMP (natural substrate) at 200 µM.

A<110%, 110%<B<130%, C>130%

The results are presented in table 3 below.

TABLE 3

| No | activity |
|---|---|
| 1 | C |
| 2 | B |
| 3 | B |
| 4 | B |
| 5 | C |
| 6 | C |
| 7 | C |
| 8 | C |
| 9 | C |
| 10 | A |
| 11 | B |
| 12 | C |
| 13 | C |
| 15 | B |
| 16 | B |
| 17 | A |
| 18 | B |
| 19 | C |
| 20 | C |
| 21 | C |

In Vivo Activity:

The following biological test allows the determination of the efficacy of compounds of formula (I) onto the control of glycemia on a pharmaceutical animal model.

All experiments on animals were carried out in accordance with the European animal care guidelines (ETS123).

Ob/ob mice from CERJ (53940 Le Genest Saint Isle, France) were treated orally with compounds of formula (1) BID during 8 days. At that time, a blood sample was collected and glucose concentration was determined using ABX diagnostic kit.

Results are given as a percentage of glycemia variation compared to an animal group control.

| Compound number | Dose | % glycemia variation |
|---|---|---|
| 12 | 150 mg/kg | −27 |
| 19 | 150 mg/kg | −41 |
| Compound 136 of WO2009/124636 | 150 mg/kg | −3 |
| Compound 202 of WO2009/124636 | 150 mg/kg | −12 |

Compounds of formula (1) clearly demonstrate their efficacy in the control of the glycemia in a diabetic animal model. Moreover, compounds of formula (1) clearly demonstrate their superiority over prior art compounds in the control of the glycemia in a diabetic animal model.

The invention claimed is:

1. A compound of formula (1)

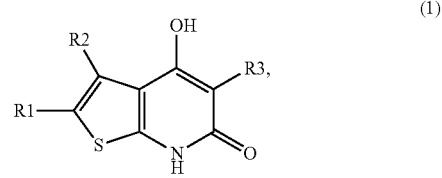

wherein:
R1 represents a hydrogen atom or a halogen atom;
R2 represents an indanyl or tetralinyl group substituted or not by one or more groups selected from halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups;
R3 represents an aryl or heteroaryl group, substituted or not by one or more atoms or groups selected from halogen atoms, alkyl groups, hydroxy, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups;
or a geometric isomer, tautomer, epimer, enantiomer, stereoisomer, diastereoisomer, racemate, pharmaceutically acceptable salt, prodrug or solvate thereof.

2. A compound according to claim 1, wherein R1 represents a halogen atom.

3. The compound according to claim 1, wherein R2 represents an indanyl group, substituted or not by one or more groups selected among halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

4. The compound according to claim 1, wherein R2 represents an tetralinyl group, substituted or not by one or more groups selected among halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

5. The compound according to claim 1, wherein R2 represents an indanyl or tetralinyl group unsubstituted or substituted by a hydroxy group.

6. The compound according to claim 1, wherein R3 represents an aryl group.

7. The compound according to claim 1, wherein R3 represents an aryl or heteroaryl group, preferably a phenyl or pyridyl group, unsubstituted or substituted by one or more atoms or groups selected from halogen atom, an alkyl, alkoxy and a cyano group.

8. A compound according to claim 1, selected from the group consisting of:
   2-chloro-4-hydroxy-3-indan-5-yl-5-phenyl-7H-thieno[2,3-b]pyridin-6-one
   2-chloro-5-(4-fluorophenyl)-4-hydroxy-3-indan-5-yl-7H-thieno[2,3-b]pyridin-6-one
   2-chloro-4-hydroxy-3-indan-5-yl-5-(3-methoxyphenyl)-7H-thieno[2,3-b]pyridin-6-one
   2-chloro-4-hydroxy-3-indan-5-yl-5-(4-methoxyphenyl)-7H-thieno[2,3-b]pyridin-6-one
   3-(2-chloro-4-hydroxy-3-indan-5-yl-6-oxo-7H-thieno[2,3-b]pyridin-5-yl)benzonitrile
   2-chloro-4-hydroxy-3-indan-5-yl-5-(3-methylphenyl)-7H-thieno[2,3-b]pyridin-6-one
   2-chloro-5-(4-fluorophenyl)-4-hydroxy-3-(4-hydroxyindan-5-yl)-7H-thieno[2,3-b]pyridin-6-one
   2-chloro-5-(3-fluorophenyl)-4-hydroxy-3-(4-hydroxyindan-5-yl)-7H-thieno[2,3-b]pyridin-6-one
   2-chloro-4-hydroxy-3-indan-5-yl-5-(3-pyridyl)-7H-thieno[2,3-b]pyridin-6-one
   2-chloro-4-hydroxy-3-(4-hydroxyindan-5-yl)-5-phenyl-7H-thieno[2,3-b]pyridin-6-one
   2-chloro-5-(2-fluorophenyl)-4-hydroxy-3-(4-hydroxyindan-5-yl)-7H-thieno[2,3-b]pyridin-6-one
   2-chloro-4-hydroxy-3-(5-hydroxytetralin-6-yl)-5-phenyl-7H-thieno[2,3-b]pyridin-6-one
   3-(2-chloro-4-hydroxy-6-oxo-3-tetralin-6-yl-7H-thieno[2,3-b]pyridin-5-yl)benzonitrile
   2-chloro-4-hydroxy-5-(3-pyridyl)-3-tetralin-6-yl-7H-thieno[2,3-b]pyridin-6-one
   Trisodium 2-chloro-3-(5-oxidotetralin-6-yl)-5-phenyl-thieno[2,3-b]pyridine-4,6-diolate
   2-chloro-4-hydroxy-5-phenyl-3-tetralin-6-yl-7H-thieno[2,3-b]pyridin-6-one
   2-chloro-5-(4-fluorophenyl)-4-hydroxy-3-(5-hydroxytetralin-6-yl)-7H-thieno[2,3-b]pyridin-6-one
   disodium 2-chloro-3-(5-oxidotetralin-6-yl)-6-oxo-5-phenyl-7H-thieno[2,3-b]pyridin-4-olate 2-chloro-4-hydroxy-3-(5-hydroxytetralin-6-yl)-5-(3-methylphenyl)-7H-thieno[2,3-b]pyridin-6-one
   2-chloro-4-hydroxy-3-(5-hydroxytetralin-6-yl)-5-(4-methyl phenyl)-7H-thieno[2,3-b]pyridin-6-one
   2-chloro-5-(3-fluorophenyl)-4-hydroxy-3-(5-hydroxytetralin-6-yl)-7H-thieno[2,3-b]pyridin-6-one
   sodium 2-chloro-3-(5-hydroxytetralin-6-yl)-6-oxo-5-phenyl-7H-thieno[2,3-b]pyridin-4-olate
   potassium 2-chloro-3-(5-hydroxytetralin-6-yl)-6-oxo-5-phenyl-7H-thieno[2,3-b]pyridin-4-olate.

9. A pharmaceutical composition comprising at least one compound according to claim 1 and a pharmaceutically acceptable support.

10. A method for treating diabetes, metabolic syndrome, obesity, liver disease, hepatic steatosis, non alcoholic fatty liver disease (NAFLD), nonalcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies, comprising administering to a subject in need thereof an effective amount of a compound according to claim 1.

* * * * *